United States Patent
Day et al.

(12)

(10) Patent No.: US 6,194,003 B1
(45) Date of Patent: Feb. 27, 2001

(54) PROCESS FOR MAKING FLURBIPROFEN LOZENGES

(75) Inventors: Andrew Day; Huw Lyn Jones; Carl Simon Smith, all of Nottingham (GB)

(73) Assignee: The Boots Company PLC, Nottingham (GB)

( * ) Notice: Subject to any disclaimer, the term of this patent is extended or adjusted under 35 U.S.C. 154(b) by 0 days.

(21) Appl. No.: 09/403,771

(22) PCT Filed: May 20, 1998

(86) PCT No.: PCT/EP98/03167

§ 371 Date: Nov. 2, 1999

§ 102(e) Date: Nov. 2, 1999

(87) PCT Pub. No.: WO98/52539

PCT Pub. Date: Nov. 26, 1998

(30) Foreign Application Priority Data

May 22, 1997 (GB) .................................................. 9710521

(51) Int. Cl.⁷ ...................................................... A61K 9/20
(52) U.S. Cl. .......................... 424/464; 424/439; 424/440; 424/489; D24/101
(58) Field of Search ..................................... 424/440, 439, 424/464, 489; D24/101

(56) References Cited

U.S. PATENT DOCUMENTS

| | | |
|---|---|---|
| 4,389,393 | 6/1983 | Schor et al. . |
| 4,666,716 * | 5/1987 | Sheth et al ........................ 424/195.1 |
| 5,302,394 | 4/1994 | Beahm . |
| 5,458,879 * | 10/1995 | Singh et al. ........................ 424/400 |
| 5,614,207 * | 3/1997 | Shah et al. ........................... 424/440 |

FOREIGN PATENT DOCUMENTS

| | | |
|---|---|---|
| 0 753 296 | 1/1997 | (EP) . |
| 92 00725 | 1/1992 | (WO) . |
| WO 97/18802 * | 5/1997 | (WO) . |

* cited by examiner

*Primary Examiner*—Thurman K. Page
*Assistant Examiner*—Liliana Di Nola-Baron
(74) *Attorney, Agent, or Firm*—Arent Fox Kintner Plotkin & Kahn, PLLC

(57) ABSTRACT

A process producing a pharmaceutical lozenge formulation comprising the steps of: 1) granulating a mixture of flurbiprofen and a bulking agent with a solution of a binding agent in a polar solvent to form granules; 2) melting a lozenge-forming composition; 3) mixing the granules with the molten lozenge-forming composition; 4) forming the resulting mixture into lozenges each containing a therapeutically effective amount of flurbiprofen.

8 Claims, No Drawings

PROCESS FOR MAKING FLURBIPROFEN LOZENGES

The present invention relates to an improved process for the preparation of pharmaceutical compositions containing flurbiprofen, said formulation being in the form of a lozenge. Flurbiprofen [2-(2-fluoro-4-biphenylyl)propionic] acid is a well known non-steroidal anti-inflammatory drug which also has analgesic and antipyretic activity. The flurbiprofen molecule exists in two enantiomeric forms and the term "flurbiprofen" as used herein is intended to embrace the individual enantiomers and mixtures thereof in any proportion including a 1:1 mixture which is herein referred to as racemic flurbiprofen. Flurbiprofen can exist in the form of pharmaceutically acceptable salts or in the form of derivatives such as esters and such salts or esters are embraced by the term flurbiprofen as used herein.

Flurbiprofen and its S(+) enantiomer have been proposed for treating medical conditions of the gums.

EP 137688-A (Upjohn) describes the use of flurbiprofen for preventing or inhibiting alveolar bone resorption.

EP 486561-A (Sepracor) describes the use of S(+)-flurbiprofen to treat periodontal disease and to promote bone regrowth associated with the disease. Periodontal disease is stated to include peridontitis, gingivitis and periodontosis.

Both these documents specifically describe the treatment of the gums and do not relate to any other part of the oral cavity.

The pharmaceutical lozenge formulations provided by the present invention are intended to be used in the treatment of sore throats by the administration to a patient in need of such treatment of the pharmaceutical lozenge composition containing a therapeutically effective amount of flurbiprofen which releases the flurbiprofen in the oral cavity so as to deliver the flurbiprofen to the surface of the sore throat.

The solid dosage form is a lozenge which is intended to be sucked by the patient. The term "lozenge" as used herein is intended to embrace all dosage forms where the product is formed by cooling a sugar-based or sugar alcohol based (eg isomalt) molten mass containing the flurbiprofen.

The therapeutically effective amount of flurbiprofen has been found to be from 5% to 40% of the normal adult dose when given by ingestion to achieve a systemic antiinflammatory and/or analgesic effect. Flurbiprofen may therefore be present in the pharmaceutical composition in an amount from 2.5 to 20 mg preferably 5 to 12.5 mg. Where a pharmaceutically acceptable salt of flurbiprofen is used, the amount of the salt used should be such as to provide the desired amount of flurbiprofen. Suitable salts include the alkali metal salts eg the sodium salt or amino acid salts eg the lysine, arginine or meglumine salts of flurbiprofen.

Flurbiprofen would be expected, in common with other non-steroidal anti-inflammatory agents, to cause an unpleasant burning sensation at the back of the mouth when retained in the mouth. This would clearly be unacceptable to the patient being treated. The present applicants have surprisingly found that an unacceptable burning sensation is not experienced when the pharmaceutical lozenge formulations provided by the present invention are used to treat a sore throat but that the patient does receive relief of the symptoms of the sore throat.

According to the present invention there is provided a process for producing a pharmaceutical lozenge formulation comprising the steps of:

1) granulating a mixture of flurbiprofen and a bulking agent with a solution of a binding agent in a polar solvent to form granules;

2) melting a lozenge-forming composition;

3) mixing the granules with the molten lozenge-forming composition;

4) forming the resulting mixture into lozenges each containing a therapeutically effective amount of flurbiprofen.

The bulking agent may be calcium carbonate, tricalcium phosphate, lactose or microcrystalline cellulose (eg as sold under the trade name Avicel). The binding agent may be polyvinylpyrrolidine and the polar solvent may be an alcoholic solvent such as industrial methylated spirit (IMS) or isopropanol (IPA). The amount of binding agent should be sufficient to ensure that the granule is robust enough not to be damaged during storage and transportation of the granule. The granule may be dried prior to blending with the molten lozenge-forming composition to remove the polar solvent. The lozenge-forming composition may be a sugar-based or sugar alcohol-based composition. If the lozenge-forming composition is sugar-based, it may comprise a single sugar (eg sucrose) or a mixture of sugars (eg a mixture of sucrose and glucose). If the lozenge-forming composition is sugar-alcohol based it may comprise sorbitol, xylitol, maltitol, maltitol syrup, lactitol, mannitol or mixtures thereof which may be in the form of the free sugar alcohols, derivatives thereof or mixtures thereof. One preferred lozenge-forming composition comprises an approximately equimolar mixture of alpha-D-gluco-pyranosyl-1,6-D-sorbitol and alpha-D-glucosopyranosyl-1,1-D-mannitol (isomalt) optionally in conjunction with a hydrogenated glucose syrup such as lycasin. The lozenge-forming composition is preferably heated to a temperature in the range of 110 to 170° C. under vacuum to remove water before the granulated components of the pharmaceutical lozenge formulation are added. The moisture content is preferably less than 2%, more preferably less than 1%. The molten mixture may be passed to individual moulds in which each lozenge is formed or may be drawn into a continuous cylindrical mass from which the individual lozenges are formed. The lozenges are then cooled, subjected to a visual check and packed into suitable packaging. One form of suitable packaging is a blister pack of a water-impermeable plastics material (eg polyvinylchloride) closed by a metallic eg aluminium foil. The patient removes the lozenge by applying pressure to the blister to force the lozenge to rupture and pass through the metal foil seal. Lozenges will normally be sucked by the patient to release the flurbiprofen.

In addition to the components listed above, the pharmaceutical lozenge formulations provided by the present invention may contain other ingredients such as acidity regulators, opacifiers, stablising agents, buffering agents, flavourings, sweeteners, colouring agents and preservatives. These additional ingredients may be dissolved in the molten lozenge-forming composition, either before or after the flurbiprofen-containing granule has been added. In another embodiment of the invention, these additional ingredients may be incorporated into the granules. If required, one or more of the additional ingredients may be encapsulated to prevent interactions with other ingredients or one or more of the additional ingredients may be included in a coating applied to the cooled lozenge.

The pharmaceutical lozenge formulations provided by the present invention are compositions which can be sucked by the patient and which slowly release the flurbiprofen. The flurbiprofen then passes over the mucous membrane of the throat where some is absorbed providing topical relief. The unabsorbed flurbiprofen is then ingested by the patient and absorbed into the blood stream. The flurbiprofen so absorbed can act systematically to provide analgesia, anti-inflammatory and anti-pyretic activity in addition to the relief that comes from the topical application of flurbiprofen to the mucous membrane of the throat.

The invention will be illustrated by the following Examples which are given by way of example only.

EXAMPLE 1

A pharmaceutical lozenge formulation is prepared containing the following components expressed in milligrams per lozenge.

| | |
|---|---|
| Racemic Flurbiprofen | 8.75 |
| Calcium Carbonate | 7.5 |
| Polyvinylpyrrolidine | 1.43 |
| Colloidal Silicon Dioxide (Aerosil) | 0.036 |
| Magnesium Stearate | 0.18 |
| Solids from a 1:1 mixture of sugar and liquid glucose | to 2350 |

The flurbiprofen and calcium carbonate are blended for two minutes and the blend granulated with a solution of the polyvinylpyrrolidine in isopropanol. The granules are dried and the colloidal silicon dioxide and magnesium stearate are added and the resulting mixture blended for five minutes. The mixture of the sugar and liquid glucose is heated to 140° C. and a vacuum applied to reduce the water content of the molten sugar lozenge base. The blended granule mixture is then added to the molten sugar lozenge base. The resulting mixture was cooled and formed into a continuous cylindrical mass from which individual lozenges are prepared.

The granules produced by the above procedure are sufficiently strong not to be damaged during transportation, show satisfactory flow properties in the process and do not stick to any of the exposed metal surfaces of the processing apparatus.

By comparison a similar process in which the flurbiprofen and calcium carbonate are not granulated but are only blended prior to being added to the molten sugar lozenge base gives a blend which had poor flow properties and thus gives rise to unacceptable variability in the content of the flurbiprofen in the resulting lozenges. A process in which the flurbiprofen and calcium carbonate are granulated with water prior to being added to the molten sugar lozenge base gives granules which are friable under the conditions in which they are being used and which have a tendency to stick to the process apparatus. The present invention therefore provides an improved process for the production of pharmaceutical lozenge formulations containing fluribprofen.

EXAMPLE 2

In a similar manner to that described in Example 1 granules are prepared which additionally contain a powdered flavouring agent. Satisfactory lozenges are produced in which the flavouring agent is not degraded and do not react with the flurbiprofen.

EXAMPLE 3

A pharmaceutical lozenge formulation is prepared containing the following components expressed in milligrams per lozenge.

| | |
|---|---|
| Racemic Flurbiprofen | 8.75 |
| Calcium Carbonate | 7.5 |
| Polyvinylpyrrolidine | 1.43 |
| Colloidal Silicon Dioxide (Aerosil) | 0.036 |
| Magnesium Stearate | 0.18 |
| Isomalt | 1885 |
| Lycasin | 440 |
| Flavouring agents | See below |

The flurbiprofen and calcium carbonate are blended for two minutes and the blend granulated with a solution of the polyvinylpyrrolidine in isopropanol. The granules are dried and the colloidal silicon dioxide and magnesium stearate are added and the resulting mixture blended for five minutes. A molten lozenge base is prepared by dissolving the isomalt in the minimum amount of water. The lycasin is added and the mixture heated at 110–120° C. The mixture is then heated to 145° C. under vacuum to remove water to give the molten lozenge base. The blended granule and the flavouring agents, which are a mixture of grapefruit (3.75 mg), orange (1.65 mg) and anise (0.348 mg) where the amounts in parenthesis are the amount of each flavour component present in each lozenge, are then added to the molten lozenge base. The resulting mixture is cooled and formed into a continuous cylindrical mass from which individual lozenges are prepared.

The granules produced by the above procedure are sufficiently strong not to be damaged during transportation, show satisfactory flow properties in the process and do not stick to any of the exposed metal surfaces of the processing apparatus.

What is claimed is:

1. A process for producing a pharmaceutical lozenge formulation comprising the steps of:
   1) granulating a mixture of flurbiprofen and a bulking agent with a solution of a binding agent in a polar solvent to form granules;
   2) melting a lozenge-forming composition;
   3) mixing the granules with the molten lozenge-forming composition;
   4) forming the resulting mixture into lozenges each containing a therapeutically effective amount of flurbiprofen.

2. A process as claimed in claim 1 wherein the bulking agent is calcium carbonate, tricalcium phosphate or microcrystalline cellulose.

3. A process as claimed in claim 1 wherein the binding agent is polyvinylpyrrolidine.

4. A process as claimed in claim 1 wherein the lozenge-forming composition comprises one or more sugars.

5. A process as claimed in claim 4 wherein the lozenge-forming compositions comprises a mixture of sucrose and glucose.

6. A process as claimed in claim 1 wherein the lozenge-forming composition comprises one or more of sorbitol, xylitol, maltitol, maltitol syrup, lactitol, mannitol or derivatives thereof.

7. A process as claimed in claim 6 wherein the lozenge-forming composition comprises an approximately equimolar mixture of alpha-D-glucopyranosyl-1,6-D-sorbitol and alpha-D-glucopyranosyl-1,1-D-mannitol.

8. A process as claimed in claim 7 wherein the lozenge-forming composition also comprises hydrogenated glucose syrup.

\* \* \* \* \*